United States Patent [19]

Kaplan et al.

[11] Patent Number: 4,588,591
[45] Date of Patent: May 13, 1986

[54] ANALGESIC 2-OXA-SPIROCYCLIC COMPOUNDS

[75] Inventors: Lester J. Kaplan, Irvine, Calif.; Moses W. McMillan, Portage, Mich.

[73] Assignee: The Upjohn Company, Kalamazoo, Mich.

[21] Appl. No.: 614,408

[22] Filed: May 25, 1984

[51] Int. Cl.$^4$ .............. A61K 31/34; A61K 31/35; C07D 307/94; C07D 311/96
[52] U.S. Cl. ................. 514/409; 260/330.3; 260/330.9; 546/15; 549/13; 549/77; 549/331; 514/326; 514/459; 514/462
[58] Field of Search ............ 424/274, 275, 267, 283, 424/285; 260/330.3, 330.9; 546/15, 407; 549/13, 77, 331

[56] References Cited
U.S. PATENT DOCUMENTS

| | | | |
|---|---|---|---|
| 4,065,573 | 12/1977 | Lednicer | 424/278 |
| 4,098,904 | 7/1978 | Szmuszkovicz | 424/324 |
| 4,145,435 | 3/1979 | Szmuszkovicz | 424/274 |
| 4,156,733 | 5/1979 | Szmuszkovicz | 424/274 |
| 4,212,878 | 7/1980 | Lednicer | 424/274 |
| 4,359,476 | 11/1982 | Kaplan et al. | 424/274 |
| 4,360,531 | 11/1982 | McMillan et al. | 424/274 |
| 4,438,130 | 3/1984 | Kaplan | 424/274 |

OTHER PUBLICATIONS

J. Org. Chem., 28, 1388 (1963), by B. T. Gillis et al.

Primary Examiner—John Kight
Assistant Examiner—M. L. Moore
Attorney, Agent, or Firm—John T. Reynolds

[57] ABSTRACT

Analgesic 2-oxa-spirocyclic compounds of the formula

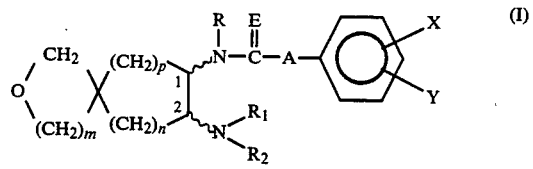

where the wavy line bonds, p, n, m, A, q, X, Y, R, R$_1$, R$_2$ and E are as defined in the specification, e.g., trans-4-bromo-N-methyl-N-[7-(1-pyrrolidinyl)-2-oxaspiro[4.5]-dec-8-yl]benzamide, and trans-3,4-dichloro-N-methyl-N-[7-(1-pyrrolidinyl)-2-oxaspiro[4.5]dec-8-yl]benzeneacetamide, and acid addition salts thereof. Pharmaceutical compositions and methods of using these compounds as analgesics are disclosed. Processes for preparing the class of compounds are also disclosed.

10 Claims, No Drawings

ANALGESIC 2-OXA-SPIROCYCLIC COMPOUNDS

INTRODUCTION

This invention relates to 2-oxa-spirocyclic-benzeneacetamide and -benzamide compounds. More particularly this invention provides some new 2-oxa-spirocyclic-phenyl-acetamide and -benzamide compounds which have useful analgesic activity, low physical dependence and abuse properties, little, if any, sedation side effects, and little, if any, dysphoria inducing properties, or which compounds are useful as chemical intermediates to such useful compounds. Processes for their preparation are disclosed. Pharmaceutical compositions and methods of use are also disclosed.

BACKGROUND OF THE INVENTION

Szmuszkovicz U.S. Pat. No. 4,145,435 discloses some cis- and trans-N-(2-aminocycloaliphatic)-2-arylacetamide derivative compounds, e.g., N-[(N',N'-dimethylamino)cyclohexyl]-N-methyl-2-(4-bromophenyl)acetamide and trans-N-methyl-N-[2-(1-pyrrolidinyl)-cyclohexyl]-2-(3,4-dichlorophenyl)acetamide, which have potent analgesic activity; the preferred compounds thereof have, in addition, only low to moderate apparent physical dependence liability compared to morphine and methadone. That Szmuszkovicz U.S. Pat. No. 4,145,435 also describes some prior art patent and publication background that may be of interest herein also.

Also, Szmuszkovicz U.S. Pat. No. 4,098,904 discloses some cis- and trans-N-(2-aminocycloaliphatic)benzamide compounds, e.g., N-methyl-N-(2-aminocycloaliphatic)benzamide compounds, e.g., N-methyl-N-[2-(1-pyrrolidinyl)cyclohexyl]-3,4-dichlorobenzamide which have potent analgesic activity, making them useful for relieving pain in warm-blooded animals. That U.S. Pat. No. 4,098,904 also discloses background patents and publications which may be of interest herein.

Lednicer U.S. Pat. No. 4,212,878, discloses some N-[(1-amino-4-(mono- or di-oxygen-group-substituted)-cyclohexyl)methyl]benzeneacetamide derivatives, e.g., 2-(3,4-dichlorophenyl)-N-[[8-(1-pyrrolidinyl)-1,4-dioxaspiro[4.5]dec-8-yl]methyl]acetamide, which also have analgesic drug properties with lower physical dependence liability characteristics than morphine or methadone. That Lednicer patent also refers to what is now Lednicer U.S. Pat. No. 4,065,573 which discloses some 4-amino-4-phenylcyclohexanone ketal compounds, e.g., 4-(m-hydroxyphenyl)-4-(dimethylamino)-cyclohexanone ethylene ketal and 4-(m-hydroxyphenyl)-4-(m-butylmethylamino)cyclohexanone ethylene ketal, which are useful for relieving pain in animals, some of which compounds exhibit narcotic antagonist activity.

McMillan et al., U.S. Pat. No. 4,360,531 discloses some N-[2-amino-(oxy-group substituted) cycloaliphatic)]phenylacetamide and -benzamide compounds, e.g., trans-3,4-dichloro-N-methyl-N-[7-(1-pyrrolidinyl)-1,4-dioxaspiro[4.5]-dec-8-yl]benzamide, and salts thereof, as analgesic compounds having low apparent physical dependence liability properties.

Kaplan et al., U.S. Pat. No. 4,359,476 discloses some N-2-amino-adjacently-oxy-substituted-cycloaliphatic-phenylacetamide and -benzamide compounds, e.g., cis- and trans-4-bromo-N-[3-methoxy-2-(1-pyrrolidinyl)cyclohexyl]-N-methylbenzamide, and cis- and trans-3,4-dichloro-N-methyl-N-[7-(1-pyrrolidinyl)-1,4-dioxaspiro[4.5]-dec-6-yl]benzamide, and salts thereof, as analgesic compounds having low apparent physical dependence liability properties.

Kaplan U.S. Pat. No. 4,438,130 discloses some 1-oxa, 1-aza and 1-thia spirocyclic benzeneacetamide and -benzamide compounds, e.g., 3,4-dichloro-N-methyl-N-[7-(1-pyrrolidinyl)-1-oxaspiro[4.5]dec-8-yl]benzeneacetamide, and salts thereof as analgesic drug compounds.

Those skilled in these chemical and pharmacology arts and sciences continue to search for new and more potent and otherwise advantageous analgesic compounds.

OBJECTS OF THE INVENTION

It is an object of this invention to provide some new spiro 2-mono-oxa ring 2-aminocyclohexylbenzeneacetamide and -benzamide compounds which are useful as analgesic drug compounds or as chemical intermediates to analgesic compounds.

It is a further object of the invention to provide new compounds of the above type which have potent analgesic properties with little or no sedative side effects and low physical dependence liability compared to morphine and methadone.

Other objects, aspects and advantages of this invention will become apparent from reading the remaining specification and the claims which follow.

SUMMARY OF THE INVENTION

Briefly, this invention provides some new mono 2-oxa- spiro ring 2-aminocyclohexyl-benzeneacetamide and -benzamide compounds, e.g., 4-bromo-N-methyl-N-[7-(1-pyrrolidinyl)-2-oxaspiro[4.5]dec-8-yl]benzamide and 3,4-dichloro-N-methyl-N-[7-(1-pyrrolidinyl)-2-oxaspiro[4.5]dec-8-yl]benzeneacetamide, and salts thereof, which have been found to have useful ranges of analgesic properties for use as pain relieving drugs in valuable warm-blooded animals, including humans, while also having little, if any, sedation side effects or physical dependence liability when administered by either the oral or parenteral routes to the warm-blooded animal or human patient in need of pain relieving treatment.

This invention also includes compounds of the above general type which may exhibit some analgesic activity of their own, but which are of some importance as chemical intermediates for the preparation of more advantageous analgesic drug compounds included herein. This invention also includes pharmaceutical compositions containing these compounds as an active analgesic component and the method of inducing analgesic activity in the animal patient, including humans, by administering one of these new compounds in an amount effective and sufficient to induce analgesic activity, regardless of origin of the pain, e.g., traumatic pain, bone pain, cancer pain, post-surgical pain, homotropic pain, menstrual pain, headache, and the like. This invention also relates to the use of these new compounds in pharmaceutical dosage unit forms, to be used, hopefully more advantageously, by the oral or parenteral administration route, for the relief of pain in valuable animals and human patients suffering pain. With more potent analgesic compounds, it should be possible to administer less of the compound to obtain a desired degree of relief from pain in the patient.

DETAILED DESCRIPTION OF THE INVENTION

More particularly, this invention provides some new 2-oxa spiro ring-N-(2-amino-substituted cyclohexyl)-benzeneacetamide and -benzamide compounds having a new chemical structure I (see GENERAL CHEMICAL STRUCTURE sheets) featuring an oxygen in the 2-position of the spiro ring.

In the compounds of Formula I, the stereochemistry at the spiro carbon atom (the carbon atom contained by both rings) can be either of the two possible orientations; the wavy line bonds between the cycloalkyl ring carbon atoms and the two nitrogen atoms indicate a cis or trans relationship of the two nitrogen-containing groups at positions 1 and 2 of the cycloalkyl ring;

p is a whole number integer 0, 1, 2, 3, or 4 and n is a whole number integer 0, 1, 2, 3 or 4 so that the resulting cycloaliphatic ring containing them has 5, 6 or 7 carbon atoms;

m is 2 or 3;

A is a single chemical bond (—), —$(CH_2)_q$— where q is a whole number integer 1 to 4 or —$CH(CH_3)$—;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino (—NHC(=O)$R_4$ wherein $R_4$ is hydrogen or $C_1$ to $C_2$-alkyl);

R is hydrogen or $C_1$ to $C_3$-alkyl;

$R_1$ and $R_2$, taken separately, are each hydrogen, $C_1$ to $C_3$-alkyl or 2-propen-1-yl; or $R_1$ and $R_2$, taken together with the nitrogen to which they are bonded complete a ring selected from the group consisting of azetidinyl, pyrrolidinyl and piperidinyl;

E is oxygen or sulfur; and the pharmacologically acceptable salts thereof.

Thus, these new compounds contain a 2-oxa-spiro ring structure attached to the 3-, 4-, 5-, 6- or 7-position of the cycloalkyl ring and an asymmetric carbon atom at such position 3, 4, 5, 6 or 7 which are not found in prior art compounds of which we are aware.

The compounds of Formula I or their acid addition salts in their crystalline state may sometimes be isolated from their reaction mixtures as solvates, i.e., with a discrete quantity of solvent, e.g., water, ethyl acetate, methanol, and the like, associated physically, and thus not affecting the chemical entity per se.

It will be recognized by those in the organic chemical art that the carbon atoms at positions 1 and 2 of the cycloalkyl ring of structure (I) to which nitrogens are bonded are asymmetrically substituted. Likewise, the cycloalkyl ring carbon atom to which the oxygn-containing ring is bonded is also asymmetrically substituted. Each of these three cycloalkyl carbon atoms can independently possess an R or S-configuration and thus a compound of the Formula (I) may have as many as $2^3$ or 8 stereoisomers which comprise four pairs of enantiomers; each enantiomeric pair is termed a racemate. See, for example, J. B. Henderickson, D. J. Cram, and G. S. Hammond, Organic Chemistry, Third Edition, McGraw-Hill Book Company, New York, N.Y., 1970, pp. 198–230, particularly pages 207, 208, 213, 215. Of the four racemates, two will have the nitrogen-containing groups at positions 1 and 2 of structure (I) in a trans orientation; that is, the groups will be on opposite sides of the plane of the cycloaliphatic ring; such compounds will be generally referred to in this specification as trans compounds and are meant to include both possible configurations of the third substituted ring carbon unless otherwise indicated. The other two racemates will have the nitrogen-containing groups at positions 1 and 2 of structure (I) in a cis orientation: that is, the groups will be the on the same side of the cycloaliphatic ring; such compounds will be generally referred to in this specification as cis compounds and are meant to include both possible configurations of the third substituted ring carbon atom unless otherwise indicated. The four racemates of structure (I) compounds each exist as a mixture of the two enantiomers or each enantiomer of each pair can be separated by conventional methods. This invention includes within its scope all enantiomeric and diastereomeric forms of the Formula I compounds either in pure form or as mixtures of enantiomers or diastereomers. In General Chemical Structure Chart A and Schemes I and II below, when a particular enantiomer or diastereomer or set of enantiomers or diastereomers is illustrated, the intent is only to convey relative stereochemistry unless otherwise indicated. When it is desired to specify for a Formula (I) compound the configuration of the other asymmetric centers relative to that of position 1, this is done according to the Chemical Abstracts Service publication, "Naming and Indexing of Chemical Substances for CHEMICAL ABSTRACTS during the Ninth Collective Period (1972–1976)," a reprint of Section IV (Selection of Index Names for Chemical Substances) from the CHEMICAL ABSTRACTS Volume 76 index Guide. Accordingly, the relative stereochemistry of three asymmetric carbon atoms in the cycloaliphatic ring of Formula I compounds is indicated by: (1) the arbitrary designation for 1α for the orientation of the substituent on (asymmetric) carbon atom number one; (2) the designation 2α or 2β when the substituent on (asymmetric) carbon atom number two is on the same or opposite side of the plane of the cycloaliphatic ring, respectively, relative to said $C_1$ substituent; and (3) the designation xα or xβ when the substituent on (asymmetric) carbon atom number x is on the same or opposite side of the plane of the cycloaliphatic ring, respectively, relative to said $C_1$ substituent.

When the stereochemistry at carbon atom number x is unknown, the designation xξ (x Xi) is used to denote either a single epimer or a mixture of epimers at carbon atom x.

Two isomers which differ only in the stereochemistry at one asymmetric carbon atom of the cycloaliphatic ring are sometimes herein referred to as epimers.

If desired, the Formula I compounds of this invention can be resolved into their respective d- and l-optical isomers by methods known in the art. In this case, the optical resolution can be done by at least two different routes. The resolving agents by either route are any of the known resolving agents such as optically active camphorsulfonic acid, bis-o-toluoyltartaric acid, tartaric acid, and diacetyl tartaric acid which are commercially available and which are commonly used for resolution of amines (bases), as for example in Organic Synthesis, Coll. Vol. V., p. 932 (1973), resolution of R-(+) and S-(—)-α-phenylethylamine with (—)-tartaric acid.

By the first method for resolving the compounds of this invention, for example, one of the aminoamide compounds (I) can be converted into its optically active diastereomeric salts by reaction with an optically active acid—examples mentioned above—in a manner standard in the isomer resolution art. These diastereomeric salts can then be separated by conventional means such as differential crystallization. Diastereomeric salts have different crystallization properties, which are taken advantage of in this separation. On neutralization of each diastereomeric salt with aqueous base the corresponding optically active enantiomers of the free amino amide can be obtained, each of which can subsequently and separately be converted as herein described to the desired acid addition salt.

By the second method, which in the case of some of these compounds is preferred, the Formula I compounds can be made into their respective d- and l-isomers, by first resolving each cis- or trans-1,2-cycloaliphatic unsymmetrically substituted amino-alcohol or diamine into its respective d- or l-isomers by treatment with the resolving agent, crystallization, separation and regeneration of the respective trans-d-diamine, trans-l-diamine, or the cis-d-diamine and cis-l-diamine, and then reacting the respective resolved diamine starting material with the desired aracyl imidazole (III) or the acyl halide (IV) or the carboxylc acid (V) to form the respective cis or trans-d- or l-compound of Formula I, which can then be converted to any desired pharmaceutically acceptable acid addition salt.

In the Formula I compounds, the halogens having atomic numbers of from 9 to 35 are fluorine, chlorine and bromine, the term "$C_1$ to $C_3$-alkyl" means methyl, ethyl, n-propyl and isopropyl.

A most significant subgroup of these Formula I compounds are those of Formula Ia wherein p is 1 or 2, n is 1 or 2, m is 2 or 3, A is a single chemical bond (—) or —$(CH_2)_q$— wherein q is 1, X and Y are each hydrogen or a halogen having an atomic number of from 9 to 35 in the 3-, 4-, or 2- or 3- and 4-positions, R is $C_1$ to $C_3$-alkyl, $R_1$ and $R_2$ are taken together with the nitrogen to which they are bonded to complete a ring selected from the group consisting of azetidinyl, pyrrolidinyl and piperidinyl, E is oxygen, and the pharmacologically acceptable salts thereof. Examples of this group of compounds include the cis- and trans-isomers of:

3,4-difluoro-N-methyl-N-[7-(1-azetidinyl)-2-oxaspiro[4.5]dec-8-yl]benzeneacetamide,
4-bromo-N-ethyl-N-[7-(1-pyrrolidinyl)-2-oxaspiro[4.5]dec-8-yl]benzeneacetamide,
3-bromo-N-(n-propyl)-N-[7-(1-piperidinyl)-2-oxaspiro[4.5]dec-8-yl]benzeneacetamide,
3,4-dichloro-N-methyl-N-[7-(1-pyrrolidinyl)-2-oxaspiro[4.5]dec-8-yl]benzeneacetamide, and the like, and the pharmacologically acceptable salts thereof.

Some further more specifically structurally identified compounds of the above type included within this invention include:

($\pm$)-(5α,6α,7β)-3,4-dichloro-N-methyl-[7-(1-pyrrolidinyl)-2-oxaspiro[4.5]dec-6-yl]benzeneacetamide,
($\pm$)-(5α,6α,7β)-3,4-dichloro-N-methyl-N-[6-(1-pyrrolidinyl)-2-oxaspiro[4.5]dec-7-yl]benzeneacetamide,
($\pm$)-(5α,6α,7β)-4-bromo-N-methyl-N-[7-(1-pyrrolidinyl)-2-oxaspiro[4.5]dec-8-yl]benzamide,
($\pm$)-(5α,7α,8β)-3,4-dichloro-N-methyl-N-[7-(1-pyrrolidinyl)-2-oxaspiro[4.5]dec-8-yl]benzamide,
($\pm$)-(5α,7α,8β)-3,4-dichloro-N-methyl-N-[8-(1-pyrrolidinyl)-2-oxaspiro[4.5]dec-7-yl]benzeneacetamide,
($\pm$)-(5α,7α,8β)-3,4-dichloro-N-methyl-N-[7-(dimethylamino)-2-oxaspiro[4.5]dec-8-yl]benzeneethanethioamide,
($\pm$)-(5α,7α,8β)-4-bromo-N-methyl-N-[7-(bis(2-propenlyl)amino)-2-oxaspiro[4.5]dec-8-yl]benzenecarbothioamide,
($\pm$)-(5α,7α,8β)-3-chloro-4-methyl-N-methyl-N-[7-(bis(n-propyl)-amino)-2-oxaspiro[4.5]dec-8-yl]benzeneacetamide,
($\pm$)-(5α,7α,8β)-4-nitro-N-methyl-N-[7-(diethylamino)-2-oxaspiro[4.5]dec-8-yl]benzamide,
3-chloro-4-methoxy-N-methyl-N-[7-(1-piperidinyl)-2-oxaspiro[4.4]non-8-yl]benzeneacetamide,
3-chloro-4-hydroxy-N-[8-(1-azetidinyl)-2-oxaspiro[5.6]undec-9-yl]benzeneacetamide, and the like.

In general, the new compounds of Formula I can be prepared by reacting the selected 1,2-cycloaliphatic diamine of Formula II, wherein the stereochemistry at the spiro carbon, the wavy line bonds, p, n, R, $R_1$, $R_2$ and m are as defined above with a suitable acyl source such as:

(1) the appropriate aracyl imidazole of Formula III wherein q, E, X and Y are as defind above;

(2) an acyl halide of Formula IV wherein M is chloride or bromide and q, E, X and Y are as defined above, in the presence of an acid scavenger such as triethylamine; or (3) the carboxylic acid of Formula V where q, E, X and Y are as defined above, in the presence of a condensing agent, in an organic solvent for the reactants, preferably in an ether solvent such as diethyl ether or a cyclic ether solvent such as tetrahydrofuran (THF) or dioxane, or the like, until the compound of the invention is produced. Carbodiimides such as dicyclohexylcarbodiimide or diisopropylcarbodiimide can be used as condensing agents.

The reactants (II) and (III) or (II) and (IV) or (II) and (V) can be mixed in substantially equimolar proportions to effect formation of the desired product (I), but if one of the reactants (II), (III), (IV) and (V) is more expensive than the other, it is sometimes preferred to use a stoichiometric excess of the less expensive reactant to insure that substantially all of the more expensive reactant is consumed in the reactions. The reaction will proceed at ambient temperature for most combinations of reactants, but for some combinations of reactants, variations from the initial to final reaction conditions may vary between $-25°$ C. and reflux temperature of the mixture depending on the reactivity of the reactants, the desired reaction time, the solvent being used, the molar proportions, and similar factors of concern to the chemist operating the process. When the new compound of this invention is to be one of Formula (I) in which one or both of $R_1$ and $R_2$ are to be hydrogen, the amino-hydrogens in the $R_1$ and/or $R_2$ positions must first be protected by procedures known in the art, then the N-protected diamine reactant (IIa) wherein the stereochemistry at the spiro carbon, the wavy line bonds, R, m, n and p are as defined for Formula II and each "—H—Q" denotes that if present, an amino hydrogen has been protected from reaction, is reacted with the selected aracyl imidazole (III) or with the acyl halide (IV) or with the carboxylic acid (V) in the presence of a condensing agent to form the N-[2-(N-protected-amino)oxa-group substituted cycloaliphatic]benzamide or -benzeneacetamide, which is then treated to remove the N-protecting group to leave as product the desired N-[2-(amino)oxa group-substituted-cycloaliphatic]benzamide or -benzeneacetamide.

Procedures for preparing the aracyl imidazoles (III) and acyl halide (IV) reactants used to form compounds of this invention are known in the art. See, for example, R. B. Wagner and H. D. Zook, SYNTHETIC ORGANIC CHEMISTRY, 1953, John Wiley and Sons, Chapter 17, p. 546 et seq. The aracyl imidazole can be prepared in situ by reacting carbonyldiimidazole with the acid of the Formula (V) in an organic solvent. Carboxylic acids of the Formula (V) are known in the art or are prepared by known methods.

Acid addition salts can be prepared by reacting a Formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicylic acid, pamoic acid, cyclohexanesulfamic acid, methanesulfonic, naphthalenesulfonic, p-toluenesulfonic, maleic, fumaric, oxalic acids and the like. The reaction can be carried out in aqueous or organic liquid solvent, non-aqueous media such as diethyl ether, ethyl acetate, and the like. Non-aqueous media are preferred. Also, whereas oxalic acid and other equivalent acids can be used to produce the aminoamide product in a more easily handled solid form, e.g., in plant manufacturing isolation procedures, it would preferably not be used as a pharmaceutically acceptable salt form of the amino-amide product. Acid addition salts of the Formula II intermediate diamines or the Formula IIa protected diamines with acids such as those named hereinabove are prepared as described for the acid addition salts of Formula I compounds herein.

As indicated generally above, the amide bond of the compounds of Formula I will be formed by the condensation of the selected diamine (II) with a carboxylic acid or acid derivative utilizing known methods. Preferred methods for this transformation are summarized in the following sets of conditions:

1. Diamine,

(where Ar denotes the

moiety), tertiary amine or equivalent amine, tetrahydrofuran (THF) or diethyl ether (Et$_2$O) and 0° C. to reflux of the mixture.

2. Diamine,

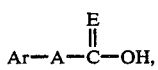

N,N'-carbonyldiimidazole, THF or Et$_2$O and 0° C. to reflux.

3. Diamine,

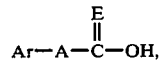

dicyclohexylcarbodiimide, THF or Et$_2$O and 0° C. to reflux.

4. Diamine,

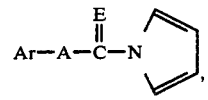

THF, or Et$_2$O and 0° C. to reflux.

5. Diamine,

tertiary amine, THF or Et$_2$O and 0° C. to reflux.

These methods require that all acidic hydrogens, which are not bonded to the nitrogen atom to be acylated, i.e., the phenolic or amino hydrogens, in the starting diamine and acid reactants be protected with a suitable protecting group.

Under certain circumstances it may be necessary to protect two (or more) different nitrogens with different protecting groups such that one such protecting group can be selectively removed while leaving the second protecting group in place. For example, the trityl and benzyl protecting groups can be used in this way, the trityl group being removable in the presence of the benzyl group under acidic conditions.

The requirements for protecting groups in Scheme I are generally well recognized by one skilled in the art of organic chemical synthesis. It is recognized that conditions for introduction and removal of protecting groups should not undesirably alter any other groups in the molecule.

Examples of suitable nitrogen protecting groups are:
 (1) benzyl (C$_6$H$_5$—CH$_2$—);
 (2) triphenylmethyl (trityl, (C$_6$H$_5$)$_3$C);
 (3) para-toluenesulfonyl (p—CH$_3$—C$_6$H$_4$—SO$_2$—); and
 (4) trialkylsilyl, for example, trimethylsilyl ((CH$_3$)$_3$Si—) or tertiary butyldimethylsilyl ((CH$_3$)$_3$Si(CH$_3$)$_2$—), and the like.
 (5) tert-butoxycarbonyl (t-BOC),
 (6) benzyloxycarbonyl,
 (7) trifluoroalkanoyl, e.g., trifluoroacetyl, trifluoropropionyl,
 (8) diphenyl(methyl)silyl,
 (9) methanesulfonyl, and the like.

Introduction and removal of such nitrogen protecting groups are well known in the art or organic chemistry: See, for example,
 (1) J. F. W. McOmie, Advances in Organic Chemistry, Vol. 3, pp. 191-281 (1963);
 (2) R. A. Boissonas, Advances in Organic Chemistry, Vol. 3, pp. 159-190 (1963);
 (3) "Protective Groups in Organic Chemistry", J. F. W. McOmie, Ed., Plenum Press, New York, 1973, p. 74, and
 (4) *Protective Groups in Organic Synthesis*, Theodora W. Greene, John Wiley and Sons, New York, 1981.

Scheme I is illustrative of the preparation of a requisite diamine starting material of the Formula II and the subsequent acylation to produce a 2-oxaspiro compound of the Formula I.

SCHEME I

In the Scheme I reactions the following comments are offered on the indicated repsective chemical step reactions.

1. The 4-carboethoxycyclohexanone, ethylene, ketal, diluted with reaction mixture solvent such as tetrahydrofuran (THF) is added slowly, say, over about 0.5 hour to a cooled (−15° C.) mixture of the lithium diisopropylamide in THF obtained by treatment of the diisopropylamine mixture with N-butyl lithium. Ethylene oxide is then slowly distilled into the cooled reaction mixture, and then the mixture is cooled for up to 16 hours and stirred to ensure completion of reaction. After cooling, the mixture is treated with an acid, e.g., 2.5N hydrochloric acid to form the 1-oxo-2-oxaspiro[4.5]decan-8-one ketal (lactone) shown at the beginning of step 2.

2. The 1-oxo-2-oxaspiro[4.5]decan-8-one ketal from step 1 (the lactone) is added slowly to a suspension of a carbonyl group reducing agent such as lithium aluminum hydride in THF in an inert atmosphere. After stirring and heating to ensure complete reaction, the mixture is cooled and excess reducing agent is decomposed. The mixture is filtered, and the filtrate is concentrated to give the intermediate ketal-diol. This ketal-diol is dissolved in a solvent, such as toluene, and treated with acid such as p-toluenesulfonic acid and refluxed to remove water to ensure complete reaction. The solvent is removed and the residue is chromatographed to obtain the desired 2-oxaspiro ketal, shown at the beginning of step 3.

3. The 2-oxaspiro ketal from step 2 is mixed with a mineral acid, e.g., 3N-hydrochloric acid solution, and an organic diluent such as acetone and stirred and warmed, say, to 55° to 60° C. for a time sufficient, say, 1 hour, to convert the ketal structure to the ketone structure, shown at the beginning of step 4.

4. The 2-oxaspiro[4.5]decan-8-one, from step 3, can be mixed in an alcohol, such as absolute ethanol and stirred under nitrogen while a reducing agent, e.g., sodium borohydride, is added. The mixture is stirred for a time sufficient to form the 2-oxaspirodecanol, shown at the beginning of step 5.

5. The 2-oxaspirodecanol is converted to an ester thereof, e.g., a p-toluenesulfonic acid ester (-OTS ester), which ester can then be added to a heated mixture of an amine, such as diazabicyclononane (DBN) to form an olefin. The mixture is heated and stirred for a time sufficient to ensure an efficient yield of the cyclo-olefin, 2-oxaspirodec-7-ene, shown at the beginning of step 6, in Scheme I.

6. The 2-oxaspirodec-7-ene can be dissolved in an appropriate solvent such as methylene chloride and treated with an epoxide forming oxidizing agent such as m-chloroperbenzoic acid in an amount and for a time sufficient to form the 7-oxabicyclo[4.1.0]heptanespiro-3,3′-(tetrahydrofuran)(epoxide) shown at the beginning of step 7.

7. The epoxide with an epoxide ring opening amine such as N-methylbenzylamine and water is heated for a time sufficient to open the epoxide ring and to form a mixture of the mixed isomers of the hydroxy-2-oxaspiro[4.5]decyl benzylamine (amino-alcohol) shown at the beginning of step 8.

8. The isomeric mixture of 2-oxaspiroamino-alcohol products from step 7 can be mixed with a tertiary amine such as triethylamine in a solvent such as methylene chloride. The mixture can be treated with methane sulfonyl chloride in methylene chloride at 0° to −20° C. After sufficient reaction time the crude methanesulfonate (mesylate) ester is isolated via extractive work-up and treated with pyrrolidine and water at 100° C. for a time sufficient to form the isomeric diamines (usually up to 20 hours). Removal of excess pyrrolidine and partitioning of the mixture between methylene chloride and water gives a brown liquid. Chromatography of the brown liquid mixture gives the isomeric diamines shown at the beginning of step 9.

9. The isomeric diamines can be deprotected such as by hydrogenation of the protected diamine in the presence of a suitable hydrogenation catalyst, e.g., palladium on carbon, in a diluent medium such as absolute ethanol at room temperature but at elevated pressure, say 20–30 psig. When the required amount of hydrogen has been consumed by the reaction mixture, the mixture can be filtered, concentrated and crystallized to obtain the N-deprotected amine mixture shown at the beginning of step 10.

10. The N-deprotected amine mixture can then be dissolved or diluted in an appropriate liquid such as diethyl ether-chloroform, mixed with an acid-scavenging amine such as triethylamine, and stirred while a selected acyl source compound such as p-bromobenzoyl chloride or 3,4-dichlorophenylacetyl chloride, which is added in excess in a diluting liquid such as ethyl ether. After stirring for a time to ensure a reasonable reaction yield, the reaction mixture can be washed with a basic aqueous solution such as 15% w/v sodium hydroxide solution, and dried. The organic solvent can be removed in vacuo and the residue can be chromatographed to separate two pure isomeric products in different fractions of the eluting solvent mixtures, such as Skellysolve ®B:isopropanol:ammonium hydroxide (95:4.7:0.3 v/v). Liquid fractions containing the respective isomer are combined and the solvents are removed in vacuo. The pure isomer product residue is taken up in an appropriate solvent such as a diethyl ether/methylene chloride/hexane mixture and crystallized therefrom.

SCHEME II

The procedure of Scheme II can be used, alternatively to the procedure in Scheme I to step 5 thereof, to prepare the shown 2-oxaspirodec-7-ene compound.

1. In step 1 of Scheme II the starting 2-oxo-3-methylene-tetrahydrofuran compound (commercially available from Aldrich Chemical Company, Catalog Number 22,641-6) can be reacted with 1,3-butadiene in a solvent such as methylene chloride at cold temperatures, say about −40° to −45° C., to control the reaction and to form the 1-oxo-2-oxaspirodec-7-ene bicyclo adduct shown as the product of step 1 in Scheme II.

2. In step 2, two chemical actions take place. The carbonyl reduction step (step 2a) can occur upon treatment of the 1-oxo-2-oxaspirodec-7-ene compound with a reducing agent, e.g., lithium aluminum hydride, to form the intermediate cyclohexene diol. In the next step, this diol can be used in crude form or after purification by known methods. In the cyclization step (step 2b) this diol can be treated with an esterifying agent such as p-toluene sulfonyl chloride to form the tosylate ester (not shown) which is intramolecularly displaced by the free hydroxyl to form the 2-oxaspirodec-7-ene as shown. The resulting 2-oxaspiro-7-ene can then be used in the Scheme I process, starting at step 6 thereof to prepare compounds of this invention.

Compounds of the Formula I wherein one of p and n is zero are prepared from the appropriate epoxide. For example, the epoxide 7-oxabicyclo[4.1.0]heptanespiro-2,3'-(tetrahydrofuran) can be used to prepare compounds of the Formula I wherein one of p and n is zero and $p+n+3=6$; this epoxide is prepared by epoxidation of 2-oxaspiro[4.5]dec-6-ene. 2-Oxaspiro[4.5]dec-6-ene is prepared from ethyl 2-oxocyclohexanecarboxylate (available from Aldrich Chemical Company) by conversion to the ketal, followed by steps analogous to those of Scheme I: alkylation of the anion alpha to the carboxylate ester with ethylene oxide, ring closure to the lactone, reduction to the diol, formation of the tosylate ester, and ring closure to the desired 2-oxaspiro[4.5]dec-6-ene.

Required starting materials are known in the art or are prepared by methods known in the art. For example, 4-carboethoxycyclohexanone, ethylene ketal is prepared as follows. Ethyl p-hydroxybenzoate (commercially available from Aldrich Chemical Company, Milwaukee, Wisc.) in ethyl alcholo is hydrogenated for 3.5 hours at 60 psi hydrogen over a 5% rhodium or alumina catalyst to produce ethyl 4-hydroxycyclohexanecarboxylate. This alcohol in methylene chloride solution is oxidized with sodium dichromate in aqueous sulfuric acid to produce ethyl 4-oxocyclohexanecarboxylate, which is also named as 4-carboethoxycyclohexanone. This ketone is reacted with ethylene glycol with paratoluenesulfonic acid as a catalyst in refluxing benzene with azeotropic removal of the water formed to produce 4-carboethoxycyclohexanone, ethylene ketal.

Other compounds of the Formula I herein are prepared by the following sequence of reactions (by general analogy to Scheme I): (1) reaction of the appropriate epoxide with an appropriate amine to form the desired intermediate amino alcohol; (2) formation of an appropriate ester, e.g., a mesylate ester, of the hydroxy group of the alcohol; (3) reaction of this amino-ester with an appropriate amine to form a desired diamine compound; and (4) reaction of the diamine with a suitable acyl source to produce the desired compound of the Formula I. By analogy with the prior art, e.g., U.S. Pat. No. 4,438,130, either the ultimate amide nitrogen or the ultimate $NR_1R_2$ nitrogen atom can be introduced first, followed by the introduction of the other.

The compounds having the nitrogen containing groups at positions 1 and 2 of structure (I) in a cis orientation are prepared by using (1) methodology herein described to construct the oxygen-containing ring, (2) methodology described in U.S. Pat. Nos. 4,360,531 and 4,359,476 described hereinabove to construct the cis diamine orientation, and (3) methodology described herein for the acylation of the cis diamines. The cis-compounds are included within the general structure I, wherein the m, n, p, A, E, R, $R_1$, $R_2$, X, and Y are as defined hereinabove.

The compounds of Formula I wherein E is to be bivalent sulfur are made by methodology disclosed in U.S. Pat. Nos. 4,360,531 and 4,359,476 referred to hereinabove.

The compounds of Formula I herein are useful as the active analgesic drug compound in pharmaceutical dosage unit forms for treating valuable mammalian animals and humans to relieve pain in that valuable animal or human. Representative Formula I analgesic drug compounds show substantial analgesic activity or potency in standard laboratory animal tests and show little, if any, sedation side effects or physical dependence liability.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the principal solvent or suspending liquid, preservatives in the nature of bacteriostatic and fungistatic agents, for example, parabens, chloro-butanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms of the compounds of this invention are prepared in accordance with the preceding general description to provide from about 0.5 to about 350 mg. of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic effects within the aforesaid effective non-toxic range. Expressed otherwise, when used systemically, an amount of the essential active ingredient is provided to a recipient within a range from about 0.01 mg./kg. to about 5 mg./kg. of body weight of the recipient.

Preferred dosages for most applications are 0.05 to 2.0 mg./kg. of body weight. In a topical semi-solid ointment formulation the concentration of the active ingredient may be 0.2–10%, preferably 0.5–5% in a carrier, such as a pharmaceutical cream base.

The useful pharmaceutical dosage unit forms of these compounds in pharmaceutical formulations are preferably adapted for systemic administration to obtain analgesic effects comprising an effective, non-toxic amount of a compound according to Formula I or as its pharmacologically acceptable salt.

Further, the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount for analgesic effects. These Formula I compounds have an advantage, to a greater extent, depending upon the particular compound, of having lower physical dependence liability than known analgesic compounds such as morphine and methadone.

Representative examples of these Formula I compounds have $ED_{50}$ values of less than about 75 mg./kg. s.c. (subcutaneous administration) in standard laboratory animal analgesic tests such as the tail flick, pinch, and hydrochloric acid or air writhing tests, and the more potent of them have $ED_{50}$ values of less than 10 mg./kg. (s.c.) in these tests. The procedures used to determine these properties of these new compounds were essentially those of Way et al., (Way, E. L. et al., "Simultaneous Quantitative Assessment of Morphine Tolerance and Physical Dependence", *J. Pharmacol. Exp. Ther.*, 167, pp. 1–8 (1969)) and Saelens et al., (Saelens, J. K. et al., The Mouse Jumping Test—A Simple Screening Method to Estimate the Physical Dependence Capacity of Analgesics", *Arch. Int. Pharmacodyn.*, 190, pp. 213–218 (1971)). Statistical effective doses ($ED_{50}$ values) and 95% confidence limits were calculated by the method of Spearman and Karber (Finney, D. J., "Statistical Methods in Biological Assay", Hafner Publ. (1952).

For example, representative preferred compounds of Formula I give low analgesic $ED_{50}$ values (less than about 10 mg. of test compound/kg. of animal body weight, subcutaneous administration route) in standard laboratory animal tests while at the same time possessing substantial freedom from apparent physical dependence liability. In contrast, known analgesic drugs such as morphine and methadone exhibit analgesic $ED_{50}$ values of less than 2 mg./kg. s.c., respectively, in these standard analgesic tail flick, pinch and writhing tests, but are known to have high apparent physical dependence liability effects, and this is confirmed by their (morphine and methadone) having relatively low naloxone jumping $ED_{50}$ values ranging from 12 to 30 mg./kg. s.c. Other representative compounds of this invention have analgesic potencies somewhat less than the preferred compounds (analgesic activity $ED_{50}$ values up to about 75 mg./kg. s.c., in these standard tests), and some such compounds still are characterized by having only low to moderate apparent physical dependence liability.

This invention is further exemplified by the following detailed examples and flow sheet schemes, the procedures of which can be used to prepare compounds of this invention, but these examples are not intended to limit the scope of the invention. All temperatures are in degrees centigrade unless otherwise noted. For brevity, Hg means mercury, bp means boiling point, $CH_2Cl_2$ means methylene chloride solvent, $K_2CO_3$, $MgSO_4$ pr $Na_2SO_4$ means the organic layer was dried over anhydrous forms of these salts, mp means melting point, NMR means a nuclear magnetic resonance spectrum, and DBN means 1,5-diazabicyclo[4.3.0]non-5-ene; h means hour(s), $N_2$ means nitrogen, TLC means thin layer chromatography procedures, $Na_2SO_3$ means sodium sulfite, $NaHCO_3$ means sodium bicarbonate, DMSO is dimethylsulfoxide, Skellysolve ®B (or Skelly B) is a tradename for a solvent of essentially n-hexane, b.p. 60°–68° C. (Merck Index, Ninth Edition (1976) page 1106), $Et_2O$ means diethyl ether, MeOH means methanol, THF means tetrahydrofuran, $H_2O$ means water, $CHCl_3$ means chloroform, brine is saturated aqueous sodium chloride solution, DMF means N,N-dimethylformamide, $Et_3N$ is triethylamine, HRMS means high resolution mass spectrum, EtOAc means ethyl acetate, GC (or g.c.) means gas chromatography, GLPC means gas liquid phase chromatography, 1 means liter(s).

EXAMPLE 1

($5\xi,7\alpha,8\beta$)-($\pm$)-4-bromo-N-methyl-N-[7-(1-pyrrolidinyl)-2-oxaspiro[4.5]dec-8-ylbenzamide, Isomers I and II A. 1-Oxo-2-oxaspiro[4.5]decan-8-one, ethylene ketal A mixture of diisopropylamine (111.3 g., 1.1 mole) in tetrahydrofuran was stirred at $-15°$ C. while n-butyl lithium was added dropwise at $-15°$ C. over 1.75 hour. Stirred the mixture for an additional 1.4 hour after the addition was completed. 4-Carboethoxycyclohexanone, ethylene ketal (210 g., 0.98 mole), diluted with tetrahydrofuran was added over ½ hour at $-15°$ C. Ethylene oxide was slowly distilled into the mixture and cooling was maintained overnight. The mixture was cooled in an ice-methanol bath and treated with 2.5N hydrochloric acid solution. The mixture was stirred ½ hour, separated into aqueous and organic phases. The aqueous phase was extracted with methylene chloride. The combined organic liquid phases were dried ($Na_2SO_4$) and solvents removed in vacuo. The residue was dissolved in diethyl ether and hexane was added to give crystal crops 1 and 2. These crops were combined and recrystallized to give 130.1 g. (55%) of the named lactone product, m.p. 95.6°–97.2° C. Mass spectrum m/e 213 (M++1); 'H-NMR, $\delta$(ppm) 1.4–2.18 (10H, multiplet); 2.20 (2H triplet); 3.96 (4H, singlet); 4.29 (2H, triplet).

B. 2-Oxaspiro[4.5]decan-8-one, ethylene ketal

A suspension of lithium aluminum hydride (95%, 47.5 g., 1.18 mole) in 600 ml. of THF was stirred under an inert atmosphere, while the lactone from part A hereinabove (242.7 g., 1.14 mole), in 2.3 liters of THF was added dropwise. The mixture was stirred overnight at ambient temperature and then heated on a steam bath for 4 hours. The mixture was cooled in an ice-water bath and the excess hydride was decomposed by addition of 45 ml. of water, 45 ml. of 15% sodium hydroxide in water solution and then 135 ml. of water. The resulting suspension was filtered, the filtrate was dried (Na$_2$SO$_4$) and concentrated in vacuo to give a pale yellow liquid, 232.2 g. (94% yield). The H-NMR spectrum was consistent with the above-named intermediate diol (not shown on Scheme I). A portion of this intermediate (179 g., 0.83 mole) was dissolved in 12 liters of toluene and p-toluenesulfonic acid monohydrate (8 g.) was added. The mixture was refluxed with water removal until the theoretical amount of water had been removed. The mixture was then stirred overnight with the heat source removed. Solvent was removed on a rotating evaporator and the resulting crude 2-oxaspiro ethylene ketal product residue (shown at the beginning of step 3 of Scheme I) (149 g.) was chromatographed to give 111.2 g. (49% yield) of the hereinabove subtitled ketal, m.p., 30°-40.6° C.

Mass spectrum m/e 198(M+); IR 930 and 1235 cm$^{-1}$(C—O—C).

The H-NMR spectrum was consistent for this named compound.

Anal. calcd. for C$_{11}$H$_{18}$O$_3$: % calcd.: C, 66.64; H, 9.15; % found: C, 66.79, H, 8.93.

C. 2-Oxaspiro[4.5]decan-8-one

A mixture of 2-oxaspiro ketal from Part B above (62 g., 0.31 mole), 0.7 liter of 3N hydrochloric acid solution, and 0.85 liter of acetone was stirred at 58° C. for one hour then stirred at ambient temperature overnight. The mixture was concentrated on a rotating evaporator and extracted with 3×500 ml. of chloroform. The resulting mixture was dried (Na$_2$SO$_4$) and concentrated in vacuo to 52.4 g. of crude material which was chromatographed on a Waters Prep 800 instrument to give 28 L g. and 19.4 g. of the above-named intermediate product (99%). IR (cm$^{-1}$), 1715 (c=o); mass spectrum m/e 154 (M+); and 'H-NMR δ (ppm) 1.70-2.20 (6H, multiplet), 2.37 (4H, triplet), 3.64 (2H, singlet), 3.90 (2H, triplet).

Anal. calcd. for C$_9$H$_{14}$O$_2$: % calcd.: C 70.10; H, 9.15; % found: C, 69.54; H, 9.43.

D. 2Oxaspiro[4.5]decan-8-ol

A mixture of 2-oxaspiro[4.5]decan-8-one (46.4 g., 0.3 mole) from Part C above in 1.5 liters of absolute ethanol was stirred under N$_2$ atmosphere while sodium borohydride was added in 1-1.5-g. portions. When the addition was completed the mixture was stirred at room temperature for 4 hours. Then 1445 ml. of water was added and stirring was continued for 30 minutes. Ethanol was removed in vacuo and the aqueous layer was extracted with chloroform to give 43 g. (91%) of a mixture of two isomers by TLC analysis and NMR spectral analysis. H-NMR δ (ppm) 1.02-1.79 (10H, multiplet); 3.24-3.95 (5H, multiplet); mass spectrum m/e 156 (M+).

Anal. calcd. for C$_9$H$_{16}$O$_2$: % calcd.: C, 69.19; H, 10.32; % found: C, 69.15; H, 11.52.

E. 2-Oxaspiro[4.5]decan-8-ol, p-toluenesulfonate (tosylate) ester

A mixture of 2-oxaspiro[4.5]decan-8-ol from Part D above (24 g., 0.154 mole), and 72 ml. of pyridine was stirred at 0° C. while p-toluenesulfonyl chloride (TsCl) (51 g.; 0.268 mole) was added in portions. After the TsCl addition was completed with the ice-water bath in place, the mixture slowly warmed to room temperature, and the mixture was stirred for three days. Water (100 ml.) was added to the mixture followed by extraction with diethyl ether. The extracts were dried with Na$_2$SO$_4$ and the ether was removed on a rotating evaporator. The mixture (pyridine and tosylate ester) was diluted with water and left standing for two days. The water was removed by filtration and the filtered solids were dried to leave the above-named intermediate product, which weighed 39.5 g. (83% yield); m.p. 68.0°-79.6° C.; mass spectrum m/e 310(M+).

Anal. calcd. for C$_{16}$H$_{22}$SO$_4$: % calcd.: C, 61.90; H, 7.14; S, 10.33; % found: C, 61.37: H, 6.97; S, 10.61.

F. 2-Oxaspiro[4.5]dec-7-ene

Method A

Diazabicyclononene (DBN) (76.2 g., 0.61 mole) was stirred and heated at 90° C. while the tosylate from Part E above (133.2 g. (0.43 mole)) was added portionwise. When the addition was completed the mixture was stirred at 110° C. for one hour then cooled in an ice-water bath. The mixture was then diluted with hexane causing the precipitation of salts. The resulting suspension was filtered and the solid filtered salts were washed with hexane. The hexane solution was concentrated on a rotating evaporator to a residue of 210 g. of a pale yellow liquid. This liquid was distilled to give 84.6 g. (74% yield) of the 2-oxaspiro[4.5]dec-7-ene as a relatively pure material which was not further purified.

H-NMR spectrum, δ (ppm): 1.45-2.25 (8H, multiplet), 3.49 (2H, singlet), 3.84 (2H, triplet), 5.65 (2H, singlet).

Method B

The diol from Example 2, Part B, hereinbelow (15.6 g.; 0.1 mole), was dissolved in 75 ml., of pyridine and cooled to −6° C. A solution of p-toluenesulfonyl chloride (20.0 g., 0.11 mole) in 84 ml. of pyridine was added slowly while maintaining the mixture temperature at about −5° C. The mixture was stirred overnight at ambient temperature, and then refluxed for five hours. Most of the pyridine was removed on a rotating evaporator and the residue was dissolved in 100 ml. of methylene chloride. The resulting solution was washed with four 50 ml. portions of 2% v/v hydrochloric acid solution. The acid wash liquids were back extracted with five 25 ml. portions of methylene chloride. The combined methylene chloride extract liquids were dried with NaSO$_4$ and concentrated to leave as a residue 11.7 g. (84.7% yield) of crude 2-oxaspiro[4.5]dec-7-ene. This intermediate product was identical to the material produced in Method A hereinabove, and was not further purified.

G. 7-Oxabicyclo[4.1.0]heptanespiro-3,3'-(tetrahydrofuran) (mixture of isomers)

A solution of 2-oxaspiro[4.5]dec-7-ene (82.8 g., 0.599 mole) from Part F, hereinabove, and 300 ml. of methylene chloride was stirred at 23°-25° C. while a solution of 80%-85% m-chloroperoxybenzoic acid in 1.59 liters of methylene chloride was added during one hour. When the addition was completed the mixture was stirred an additional hour before excess peroxy acid was neutralized by addition of 150 ml. of 10% sodium bisulfite solution. The suspension was filtered through a filter aid (CELITE ®) bed and the filtrate was washed with 3×500 ml. portions of 10% w/v sodium hydroxide solution followed by a 500-ml. water wash. Solvent was removed by evaporation to give 98.1 g. of a crude mixture of epoxide isomers. Vacuum-distillation at 71°-75° C./40 μHg. gave 67.1 g. of the subtitled epoxide mixture. Another 2.3 g. of the expoxide was obtained by redistillation of the pot residue and an earlier fraction; combined yield 69.4 g. (75.1%). Mass spectrum m/e 154 (M+) and H-NMR were consistent with the structure assignment.

Anal. Calcd for $C_9H_{14}O_2$: % calcd: C, 7.10; H, 9.15; % found: C, 70.09; H, 8.86.

H. Trans(±)-7-(N-methyl-N-benzylamino)-8-hydroxy-2-oxaspiro[4.5]decane and trans(±)-7-hydroxy-8-(N-methyl-N-benzylamino)-2-oxaspiro[4.5]decane (mixture of isomers)

The epoxide mixture from Part G above (65 g., 0.42 mole), N-methyl benzylamine (69.8 g., 0.58 mole), and water (49 ml.) were heated and stirred at 95° C. for 113 hours; all epoxide had been consumed. The mixture was stirred while it cooled to room temperature, and the mixture was then let stand without stirring. The liquid phases were separated and the aqueous phase was extracted with 3×25 ml. portions of methylene chloride. The combined organic phases were dried ($Na_2SO_4$) and solvents removed on the rotating evaporator. The oil solidified on standing overnight. The solid was dissolved in hot hexane and slowly cooled to −6° C. to give 72.5 g. (62.5%) of the above-named mixed isomers. Further purification of the mother liquors gave an additional 22.6 g. Total yield of the white solid subtitled isomer mixture is 95.1 g. (81.9%), m.p. 62.5°–68.9° C. Mass spectrum m/e 275 (M+), 'H-NMR $CDCl_3$, δ (ppm), 1.1–2.5 (12H, multiplet), 3.2–3.73 (8H, multiplet), 3.79 (2H, triplet), 7.23 (5H, singlet).

Calcd. for $C_{17}H_{25}NO_2$: % calcd: C, 74.14; H, 9.15; N, 5.09; % found: C, 73.85; H, 9.12; N, 5.06.

I. Trans(±)-7-(N-methyl(benzylamino))-8-(1-pyrrolidinyl)-2-oxaspiro[4.5]decane and trans(±)-8-(N-methyl(benzylamino))-7-(1-pyrrolidinyl)-2-oxaspiro[4.5]decane The mixture of isomeric 2-oxaspiro amino alcohols from Part H above (17.1 g., 0.062 mole) and triethylamine (8.9 g., 0.088 mole) were dissolved in 149 ml. of methylene chloride and stirred while being cooled in an ice-methanol bath. Methanesulfonyl chloride (14.4 g., 0.126 mole) in 28 ml. of methylene chloride was added dropwise. When the addition was completed the mixture was stirred for about 17 hours. The mixture was cooled in an ice-water bath, 50 ml. of water was added, and the mixtures stirred for one hour with the bath removed. The phases were separated, the methylene chloride phase was washed with saturated aqueous sodium bicarbonate, separated from the aqueous phase and dried ($Na_2SO_4$). Concentration of the dried solution on an evaporator gave a mixture of crude mesylate esters. The crude mesylate ester mixture was stirred for 19.5 hours with 118 ml. of pyrrolidine and 16 ml. of water at 100° C. Some pyrrolidine was removed on the evaporator, chloroform was added and the aqueous layer was removed. The chloroform solution was dried ($Na_2SO_4$) and concentrated on the evaporator to give 38.2 of brown liquid. The brown liquid material was chromatographed on 2.3 kg. of silica gel with methylene chloride:methanol:ammonium hydroxide (94:5:1) eluate to give three main fractions. Fractions 1 and 2 gave 7.5 g. (36.8%) of solid from ethyl acetate-methylene chloride. Fraction 3 gave 7.2 g. (35%) of an oil which would not crystallize. 'H-NMR spectral analysis of the solid from fractions 1 and 2 supported the production of a mixture of the subtitled isomeric diamines.

J. (5ξ,7α,8β)-(±)-4-Bromo-N-methyl-N-[7-(1-pyrrolidinyl)-2-oxaspiro[4.5dec-8-yl]benzamides, Isomers I and II A mixture of isomeric diamines from Part I above (7.35 g., 0.022 mole), 10% palladium on carbon, and 100 ml. of absolute ethanol was stirred at room temperature and 25 p.s.i. of hydrogen until slightly more than the required amount of hydrogen had been consumed; the diamino starting material had been consumed at this point and replaced by two non-UV-active spots on TLC. The resulting suspension was filtered through a filter aid and concentrated on the evaporator. Crystallization from ethyl acetate-hexane and drying gave 3.4 g. (64%) of a mixture of isomeric deprotected diamines. The deprotected diamine mixture (2.9 g., 0.012 mole), triethylamine (3.8 g., 0.037 mole), ethyl ether (75 ml.), and chloroform (50 ml.) was stirred at room temperature while excess p-bromobenzoyl chloride in 7.5 ml. of ethyl ether was added dropwise. After the addition was completed the mixture was stirred for 41 hours. The resulting suspension was washed with two 68 ml. portions of 15% sodium hydroxide solution and dried ($Na_2SO_4$). The solvent was removed in vacuo to give 10.1 g. of crude material. The crude material was chromatographed on a 500 g. (silica gel) medium pressure column with Skellysolve ®B:i-propanol:ammonium hydroxide (95:4.7:0.3). Fractions containing pure Isomer I were combined and solvents were removed in vacuo. Crystallization from ethermethylene chloride-hexane gave white needles (1.1 g., 21%) after drying. Isomer I had m.p. 167.5°–170.3° C. and mass spectrum m/e 421 (M+) along with m/e 166 ($C_{10}H_{16}NO^+$) which fixes the position of the pyrrolidinyl group on the cyclohexane ring at C-7.

Anal. Calcd. for $C_{21}H_{29}BrN_2O_2$: % calcd: C, 59.85; H, 6.94; Br, 18.97; N, 6.65; % found: C, 59.70; H, 6.91; Br, 18.99; N, 6.64.

Fractions containing pure Isomer II were combined and solvents removed in vacuo. Crystallization from hot methylene chloride-hexane gave white needles (1.3 g., 25%) Isomer II had m.p. 130.1°–135.3° C. and mass spectrum m/e 421 (M+) along with m/e 166 ($C_{10}H_{16}NO^+$) again fixing the position of the pyrrolidinyl group on the cyclohexane ring at C-7.

Anal. Calcd. for $C_{21}H_{29}BrN_2O_2$: % calcd: C, 59.85; H, 6.94; Br, 18.97; N, 6.65; % found: C, 59.75; H, 6.86; Br, 18.46; N, 6.56.

EXAMPLE 2

4-(Hydroxymethyl-4-(2'-hydroxyethyl)-cyclohex-1-ene (an intermediate)

A. 1-Oxo-2-oxaspiro[4.5]dec-7-ene

Methylene chloride (5.3 liters) was stirred and cooled in a 12-l, 3-neck, round-bottom flask using a dry ice-acetonitrile cooling bath. α-Methylene-γ-butyrolactone (142.9 g., 1.46 mole) was added, followed by the protion-wise addition of aluminum chloride (197 g., 1.48 mole). The mixture was stirred about 20 minutes until the yellow complexion color appeared. A cylinder of butadiene was cooled in a dry ice-acetone bath and the entire contents of the cylinder (170 g., 3.14 mole) was added from the inverted cylinder past a cold finger into the reaction mixture. A Dewar condenser cooled with dry ice-acetone was used to prevent butadiene escaping as a gas. The mixture was stirred overnight with the cooling bath and condenser in place while the mixture slowly warmed to room temperature. Additional butadiene (150 g., 2.77 mole) was added and the mixture was again stirred overnight; all of the starting lactone had been consumed. Excess aluminum chloride was decomposed by the slow addition of 1.74 liters of water. The resulting mixture was filtered through a bed of filter aid (CELITE ®). The polymeric material deposited on the filter aid was slurried in 0.75 liters of methanol, stirred for 20 minutes, filtered and set aside. The original filtrate was separated and the aqueous phase extracted with an additional 1.0 liter of methylene chloride. The combined organic extracts were dried ($Na_2SO_4$) and filtered. To this solution was added 1.0 liter of methanol along with the methanol filtrates above. The mixture was stirred for about 20 minutes, then filtered through a filter aid (CELITE®) again. Concentration on the evaporator caused more polymer to precipitate; this was removed by filtration. A final concentration in vacuo gave an oil. To this oil was added a similar residue obtained from 41 g. (0.42 mole) of α-methylene-γ-butyrolactone. Distillation on a Kugelrohr apparatus at 80° C. and 0.35 mm. Hg. gave 236.1 g. (82.5%) of the above-named intermediate product containing 0.21% of water. Mass spectrum m/e 152 ($M^+$), m/e 108$M^+$—$CO_2$), m/e 93 (m/e 108—$CH_3$.), and m/e 79 ($M^+$—$CO_2$, $CH_3CH_2$.).

Anal. Calcd. for $C_9H_{12}O_2$.0.21% $H_2O$: % calcd: C, 71.03; H, 7.95; % found: C, 70.91; H, 7.68.

B. 4-(Hydroxymethyl)-4-(2'-hydroxyethyl)cyclohex-1-ene

Lithium aluminum hydride (2.38 g., 0.063 mole) was suspended in 37.7 ml. of tetrahydrofuran and stirred while the olefinic lactone from Part A hereinabove (15.2 g., 0.1 mole) in 143 ml. of tetrahydrofuran was added slowly. The mixture was stirred at ambient temperature for three days then refluxed for 10 hours. The mixture was cooled in an ice-methanol bath and then 2.38 ml. of water, followed by 2.38 ml. of 15% sodium hydroxide solution, and finally 7.14 ml. of water were added. The mixture was stirred overnight at ambient temperature. The precipitate which resulted was filtered through a bed of filter aid (CELITE®) and the precipitate was washed well with methylene chloride and then filtered. The combined filtrates were concentrated to a liquid on the evaporator. Distillation on a Kugelrohr apparatus at 85°-100° C. and 0.01 mm. Hg. gave 8.8 g. (56%) of the subtitled diol. Mass spectrum CI ($NH_3$) gave m/e 330 ($2M^+ + NH_4$), m/e 313 ($2M^+ + H$), and m/e 174 ($M^+ + NH_4$); 'H-NMR supported the structure assignment.

Anal. Calcd. for $C_9H_{16}O_2$: % calcd: C, 69.19; H, 10.32; % found: C, 68.96; H, 10.07.

EXAMPLE 3

(5ξ,7α,8β)-(±)-3,4-Dichloro-N-methyl-N-[7-(1-pyrrolidinyl)-2-oxaspiro[4.5]dec-8-yl]benzeneacetamide, Isomers I and II To a solution of 7.5 g. of 3,4-dichlorophenyl acetic acid in 250 ml. of dry tetrahydrofuran there was added 5.9 g. of 1,1'-carbonyldiimidazole, and the resultant mixture was stirred at ambient temperature for one hour. A solution of 7.5 g. of the mixture of isomeric diamines from Example 1, Part I above in 200 ml. of dry THF is added dropwise, and the resultant mixture is stirred at ambient temperature for 18 hours. The bulk of the THF is removed on a rotary evaporator and the residue is distributed between diethyl ether and water. The liquid phases are separated and the ether phase was washed once with water, once with brine, dried ($MgSO_4$) and concentrated to give the crude amino-amide product mixture. Chromatographic purification generally as described above in Example 1, Part J provides the titled amino-amide Isomers I and II.

EXAMPLE 4

One thousand tablets for oral use, each containing 40 mg. of trans-4-bromo-N-methyl-N-[7-(1-pyrrolidinyl)-2-oxaspiro[4.5]dec-8-yl]benzamide Isomer I hydrochloride as the essential active ingredient are prepared from the following ingredients Essential active ingredient: 40 gm.
Dicalcium phosphate: 150 gm.
Methylcellulose, USP (15 cps.): 6.5 gm.
Talc: 20 gm.
Calcium stearate: 2.0 gm.

The essential active ingredient and dicalcium phosphate are mixed well, granulated with 7.5% aqueous solution of methylcellulose, passed through a No. 8 screen and dried carefully. The dried granules are passed through a No. 12 screen, mixed with the talc and stearate and compressed into tablets. These tablets are useful in the treatment of low back pain in adult humans at a dose of 1 tablet 1–4 times a day as needed.

EXAMPLE 5

One thousand two-piece hard gelatin capsules for oral use, each capsule containing 20 mg. of trans-3,4-dichloro-N-methyl-N-[7-(1-pyrrolidinyl)-2-oxaspiro[4.5]dec-8-yl]benzeneacetamide Isomer I succinate as the essential active ingredient are prepared from the following ingredients:

Essential active ingredient: 20 gm.
Lactose, USP: 100 gm.
Starch, USP: 10 gm.
Talc, USP: 5 gm.
Calcium stearate: 1 gm.

The finely powdered materials are mixed thoroughly, then filled into hard gelatin capsules of appropriate size.

One capsule 4 times daily is useful for the treatment of dental pain in adult humans.

EXAMPLE 6

One-piece soft elastic capsules for oral use, each containing 100 mg. of trans(−)-4-bromo-N-methyl-N-[7-(1-pyrrolidinyl)-2-oxaspiro[4.5]dec-8-yl]benzamide Isomer I maleate as the essential active ingredient are prepared in the usual manner by first dispersing the active material in sufficient corn oil to render the material capsulatable.

One capsule two times daily is useful in the treatment of pain in adult humans.

EXAMPLE 7

An aqueous oral preparation containing in each teaspoonful (5 ml.) 80 mg. of trans(31)-4-bromo-N-methyl-N-[7-(1-pyrrolidinyl)-2-oxaspiro[4.5]dec-8-yl]benzamide Isomer II maleate as the essential active ingredient is prepared from the following ingredients:

Essential active ingredient: 160 gm.
Methylparaben, USP: 7.5 gm.
Propylparaben, USP: 2.5 gm.
Saccharin: 12.5 gm.
Glycerine: 3,000 ml.
Tragacanth powder: 10 gm.
Orange oil flavor: 10 gm.
Orange II: 7.5 gm.
Deionized water, q.s. to: 10,000 ml.

The foregoing aqueous preparation is useful in the treatment of adult pain due to muscle spasm at a dose of 1 teaspoonful 4 times daily.

EXAMPLE 8

One thousand tablets for oral administration, each containing 10 mg. of trans(−)-4-bromo-N-methyl-N-[7-(1-pyrrolidinyl)-2-oxaspiro[4.5]dec-8-yl]benzamide Isomer I maleate as the essential active ingredient are prepared from the following ingredients:

Essential active ingredient, micronized: 10 gm.
Lactose: 150 gm.
Starch: 15 gm.
Magnesium stearate: 1.5 gm.

The ingredients are thoroughly mixed and slugged. The slugs are broken down by forcing through a screen and the resulting granules are then compressed into tablets.

These tablets are useful in reducing post-surgical pain in dogs at a dose of 1–3 tablets depending on the weight of the animal and its condition.

EXAMPLE 9

A sterile aqueous suspension suitable for intramuscular injection and containing in each milliliter 50 mg. of trans(+)-3,4-dichloro-N-methyl-N-[7-(1-pyrrolidinyl)-2-oxaspiro[4.5]dec-8-yl]benzeneacetamide Isomer II phosphate as the essential active ingredient is prepared from the following ingredients:

Essential active ingredient: 5 gm.
Polyethylene glycol 4000, USP: 3 gm.
Sodium chloride: 0.9 gm.
Polysorbate 80, USP: 0.4 gm.
Sodium metabisulfite: 0.1 gm.
Methylparaben, USP: 0.18 gm.
Propylparaben, USP: 0.02 gm.
Water for injection, q.s. to 100 ml.

The preceding sterile injectable is useful in the treatment of pain at a dose of one-half to 2 ml.

(A) GENERAL CHEMICAL STRUCTURES

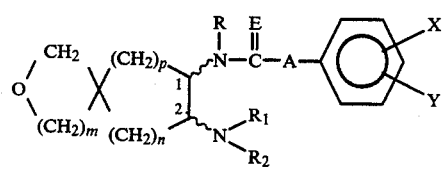

(I)

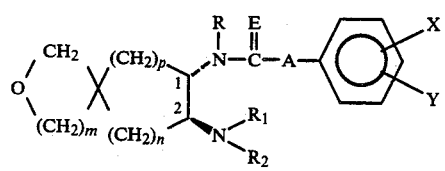

(Ia)

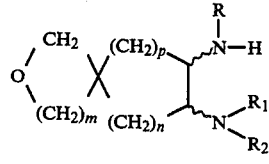

(II)

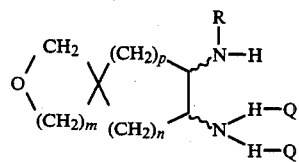

(IIa)

-continued
(A) GENERAL CHEMICAL STRUCTURES

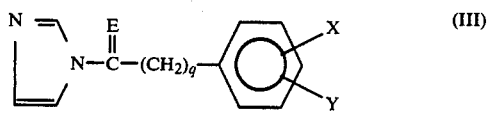

(III)

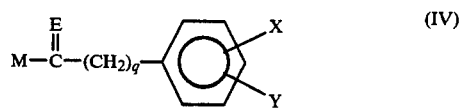

(IV)

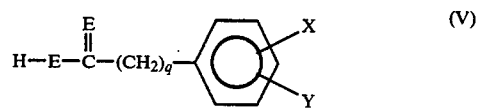

(V)

SCHEME I

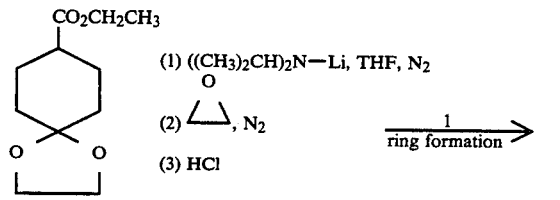

(1) $((CH_3)_2CH)_2N-Li$, THF, $N_2$
(2) △, $N_2$
(3) HCl

→ 1 ring formation

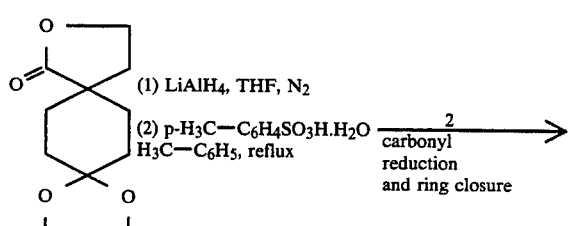

(1) $LiAlH_4$, THF, $N_2$
(2) $p-H_3C-C_6H_4SO_3H \cdot H_2O$
$H_3C-C_6H_5$, reflux → 2 carbonyl reduction and ring closure

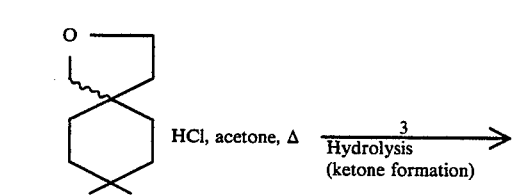

HCl, acetone, Δ

→ 3 Hydrolysis (ketone formation)

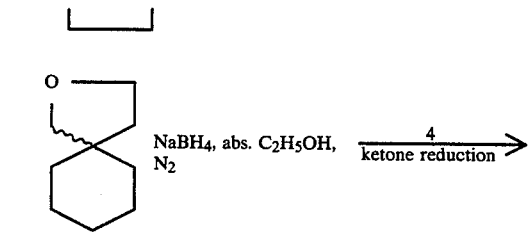

$NaBH_4$, abs. $C_2H_5OH$, $N_2$

→ 4 ketone reduction

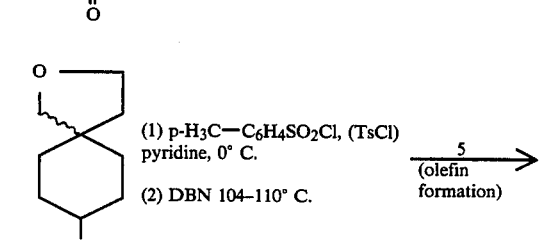

(1) $p-H_3C-C_6H_4SO_2Cl$, (TsCl) pyridine, 0° C.
(2) DBN 104–110° C.

→ 5 (olefin formation)

-continued
SCHEME I
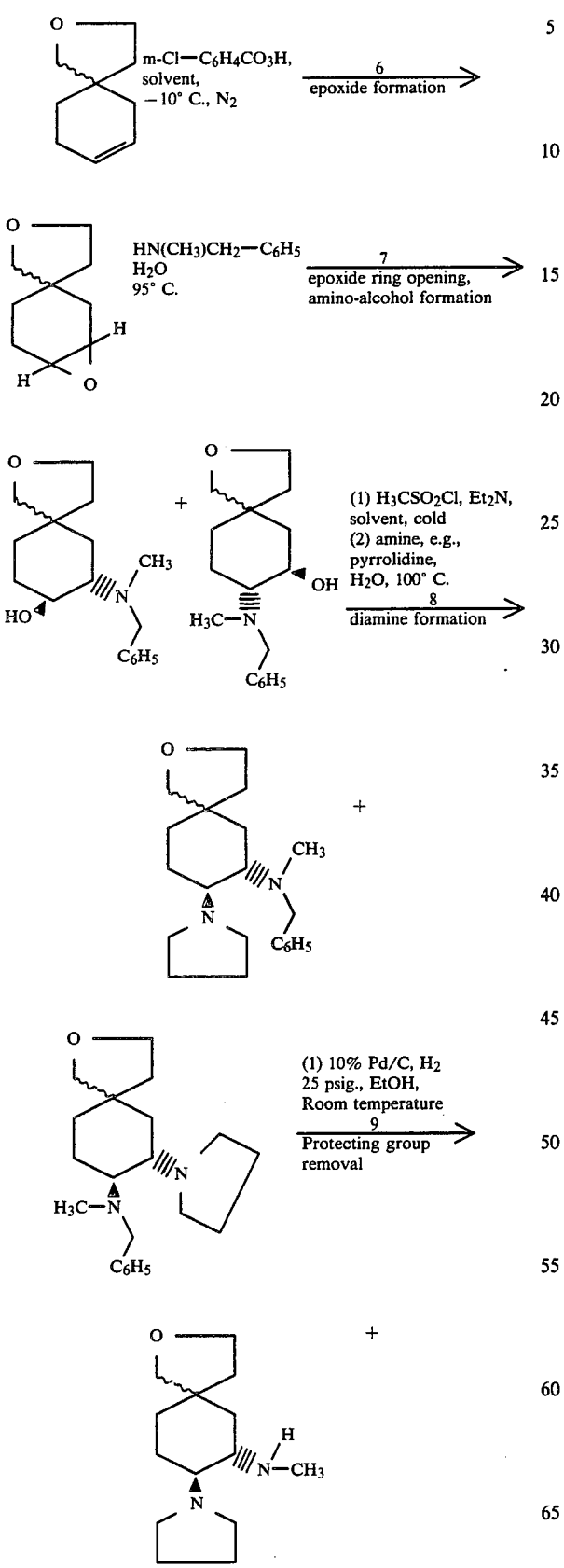
-continued
SCHEME I
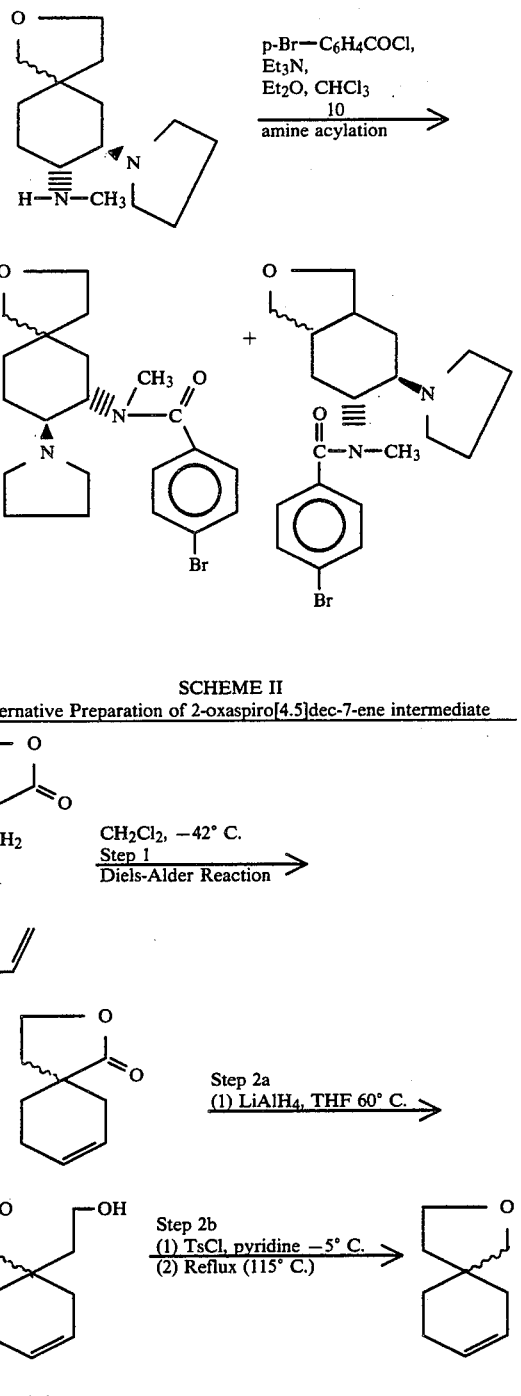
SCHEME II
Alternative Preparation of 2-oxaspiro[4.5]dec-7-ene intermediate
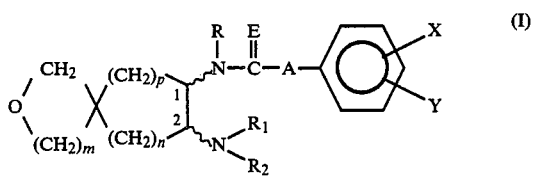
We claim:
1. A compound of the formula
$$\text{(I)}$$
wherein the stereochemistry at the spiro carbon atom is either of the two possible orientations;

the wavy line bonds between the cycloalkyl ring carbon atoms and the two nitrogen atoms indicate a cis or trans relationship of the two nitrogen-containing groups at positions 1 and 2 of the cycloalkyl ring;

wherein p is a whole number integer 0, 1, 2, 3 or 4 and n is a whole number integer 0, 1, 2, 3, or 4 so that the resulting cycloaliphatic ring containing them has 5, 6 or 7 carbon atoms;

m is 2 or 3;

A is a single chemical bond (—), —$(CH_2)_q$ where q is a whole number integer 1 to 4 or —$CH(CH_3)$—;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino (—NHC($=$O)$R_4$ wherein $R_4$ is hydrogen or $C_1$ to $C_2$-alkyl);

R is hydrogen or $C_1$ to $C_3$-alkyl;

$R_1$ and $R_2$, taken separately, are each hydrogen, $C_1$ to $C_3$-alkyl or 2-propen-1-yl; or $R_1$ and $R_2$, taken together with the nitrogen to which they are bonded complete a ring selected from the group consisting of azetidinyl, pyrrolidinyl and piperidinyl;

E is oxygen or sulfur; or a pharmacologically acceptable salt thereof.

2. A compound according to claim 1 wherein p is 1 or 2, n is 1 or 2;

m is 2 or 3;

A is a single chemical bond (—) or $(CH_2)_q$ where q is a whole number 1;

X and Y are independently hydrogen or a halogen having an atomic number of from 9 to 35;

R is $C_1$ to $C_3$-alkyl;

$R_1$ and $R_2$ are taken together with the nitrogen to which they are bonded to complete a ring selected from the group consisting of azetidinyl, pyrrolidinyl and piperidinyl;

E is oxygen; or a pharmacologically acceptable salt thereof.

3. A compound according to claim 2 which is 4-bromo-N-methyl-N-[7-(1-pyrrolidinyl)-2-oxaspiro[4.5]-dec-8-yl]benzamide, or a pharmacologically acceptable salt thereof.

4. A compound according to claim 2 which is 3,4-dichloro-N-methyl-N-[7-(1-pyrrolidinyl)-2-oxaspiro[4.5]dec-8-yl]benzeneacetamide, or a pharmacologically acceptable salt thereof.

5. A composition useful in pharmaceutically effective dosage unit form for alleviating pain in a warm-blooded animal which comprises a compound of claim 1 in combination with a pharmaceutically acceptable carrier.

6. A composition according to claim 5 wherein the compound of claim 1 is a trans-4-bromo-N-methyl-N-[7-(1-pyrrolidinyl)-2-oxaspiro[4.5]dec-8-yl]benzamide, or a pharmaceutically acceptable salt thereof.

7. A method of alleviating pain which comprises administering to a valuable warm-blooded animal suffering pain an analgesically effective amount of a compound according to claim 1 in a pharmaceutical dosage unit form.

8. A method according to claim 7 wherein the analgesic compound is a trans-4-bromo-N-methyl-N-[7-(1-pyrrolidinyl)-2-oxaspiro[4.5]dec-8-yl]benzamide, or a pharmaceutically acceptable salt thereof.

9. A compound of the formula

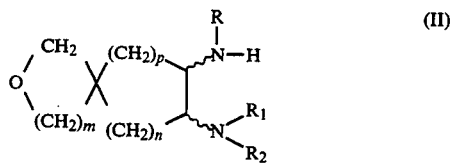

(II)

wherein the stereochemistry at the spiro carbon atom can be either of two possible orientations;

the wavy line bonds between the cycloalkyl ring carbon atoms and the two nitrogen atoms indicate a cis- or trans-relationship of the two nitrogen containing groups at positions 1- and 2- of the cycloalkyl ring;

p is a whole number integer 0, 1, 2, 3 or 4 and n is a whole number integer 0, 1, 2, 3 or 4 so that the resulting cycloaliphatic ring containing them has 5, 6 or 7 carbon atoms;

m is 2 or 3;

R is hydrogen or $C_1$ to $C_3$-alkyl;

$R_1$ and $R_2$, taken separately, are each hydrogen, $C_1$ to $C_3$-alkyl or 2-propen-1-yl; or $R_1$ and $R_2$, taken together with the nitrogen to which they are bonded complete a ring selected from the group consisting of azetidinyl, pyrrolidinyl and piperidinyl;

and N-(protected amino) derivatives thereof;

and acid addition salts thereof.

10. A compound according to claim 9 which is a mixture of trans($\pm$)-7-(N-methyl(benzylamino))-8-(1-pyrrolidinyl)-2-oxaspiro[4.5]decane and trans($\pm$)-8-(N-methyl(benzylamino)-7-(1-pyrrolidinyl)-2-oxaspiro[4.5]decane.

* * * * *